United States Patent [19]
Honeycutt

[11] Patent Number: 5,871,679
[45] Date of Patent: Feb. 16, 1999

[54] METHOD OF PRODUCING HOT WATER SOLUBLE GARMENTS AND LIKE FABRICS

[75] Inventor: Travis W. Honeycutt, Gainesville, Ga.

[73] Assignee: Isolyser Company, Inc., Norcross, Ga.

[21] Appl. No.: 970,182

[22] Filed: Nov. 14, 1997

Related U.S. Application Data

[63] Continuation of Ser. No. 618,008, Mar. 18, 1996, abandoned, which is a continuation of Ser. No. 299,760, Sep. 1, 1994, which is a continuation of Ser. No. 55,083, Apr. 29, 1993, abandoned, which is a continuation-in-part of Ser. No. 881,685, May 12, 1992, Pat. No. 5,207,837, which is a continuation-in-part of Ser. No. 683,290, Apr. 10, 1991, abandoned.

[51] Int. Cl.$^6$ ........................................................ D01F 6/14
[52] U.S. Cl. ........................ 264/185; 264/211; 264/216; 264/563
[58] Field of Search .................................... 264/185, 211, 264/216, 563

[56] References Cited

U.S. PATENT DOCUMENTS

| | | |
|---|---|---|
| 2,340,866 | 2/1944 | Dangelmajer . |
| 2,395,616 | 2/1946 | Dangelmajer . |
| 2,408,377 | 10/1946 | Dangelmajer . |
| 2,430,949 | 11/1947 | Porter et al. . |
| 2,909,502 | 10/1959 | Matsumoto et al. . |
| 3,089,493 | 5/1963 | Galindo . |
| 3,314,809 | 4/1967 | Klug . |
| 3,372,311 | 3/1968 | Lobur . |
| 3,413,229 | 11/1968 | Bianco et al. . |
| 3,484,874 | 12/1969 | Bickenheuser . |
| 3,578,619 | 5/1971 | Reeder . |
| 3,607,812 | 9/1971 | Takigawa et al. . |
| 3,637,657 | 1/1972 | Morii et al. . |
| 3,762,454 | 10/1973 | Wilkins . |
| 3,790,067 | 2/1974 | Scheier . |
| 3,859,125 | 1/1975 | Miller et al. . |
| 3,865,918 | 2/1975 | Mitchell et al. . |
| 3,886,112 | 5/1975 | Watson et al. . |
| 3,886,610 | 6/1975 | Shelden . |
| 3,930,086 | 12/1975 | Harmon . |
| 3,931,088 | 1/1976 | Sakurada et al. . |
| 4,073,733 | 2/1978 | Yamauchi et al. . |
| 4,079,036 | 3/1978 | Ohmori et al. . |
| 4,258,849 | 3/1981 | Miller . |
| 4,279,752 | 7/1981 | Sueoka et al. . |
| 4,295,850 | 10/1981 | Haberli et al. . |
| 4,309,494 | 1/1982 | Stocken . |
| 4,343,133 | 8/1982 | Daniels et al. . |
| 4,478,971 | 10/1984 | Ballard . |
| 4,536,532 | 8/1985 | Miller et al. . |
| 4,568,341 | 2/1986 | Mitchell et al. . |
| 4,612,157 | 9/1986 | Genba et al. . |
| 4,619,793 | 10/1986 | Lee . |
| 4,620,999 | 11/1986 | Holmes . |
| 4,651,725 | 3/1987 | Kifune et al. . |
| 4,863,779 | 9/1989 | Damponte . |
| 4,952,550 | 8/1990 | Wallach et al. . |
| 4,959,341 | 9/1990 | Wallach . |
| 4,959,464 | 9/1990 | Yeh . |
| 4,971,861 | 11/1990 | Watanabe et al. . |
| 5,051,222 | 9/1991 | Marten et al. . |
| 5,106,890 | 4/1992 | Maruhashi et al. . |
| 5,181,966 | 1/1993 | Honeycutt et al. . |
| 5,181,967 | 1/1993 | Honeycutt . |
| 5,183,571 | 2/1993 | Hanel et al. . |
| 5,207,837 | 5/1993 | Honeycutt . |
| 5,208,104 | 5/1993 | Uda et al. . |
| 5,225,120 | 7/1993 | Graiver et al. . |
| 5,252,340 | 10/1993 | Honeycutt . |
| 5,268,222 | 12/1993 | Honeycutt . |
| 5,620,786 | 4/1997 | Honeycutt et al. . |

FOREIGN PATENT DOCUMENTS

| | | |
|---|---|---|
| 8902229 | 1/1990 | Brazil . |
| 010171 | 4/1980 | European Pat. Off. . |
| 0050288 | 4/1982 | European Pat. Off. . |
| 0107576 | 5/1984 | European Pat. Off. . |
| 0176316 | 4/1986 | European Pat. Off. . |
| 0272816 | 6/1988 | European Pat. Off. . |
| 0320895 | 12/1988 | European Pat. Off. . |
| 15 19 530 | 1/1963 | Germany . |
| 30 17 246 | 11/1981 | Germany . |
| 386161 | 1/1933 | United Kingdom . |
| 743165 | 1/1956 | United Kingdom . |
| 1187690 | 4/1970 | United Kingdom . |
| 1271424 | 4/1972 | United Kingdom . |
| 1312370 | 4/1973 | United Kingdom . |
| 1374199 | 11/1974 | United Kingdom . |
| 1451619 | 10/1976 | United Kingdom . |
| 2083762 | 3/1982 | United Kingdom . |

*Primary Examiner*—James J. Bell
*Attorney, Agent, or Firm*—Needle & Rosenberg, P.C.

[57] ABSTRACT

A method of disposing of garments after use. The garments, linens, drapes, towels and other useful articles are provided as woven, non-woven, knitted or otherwise formed fabric of thermoplastic polyvinyl alcohol polymer fiber, the fiber being water soluble only at temperatures above approximately 37° C. and preferably above 50° C. After use, the fabric is subjected to water at a sufficient temperature to substantially dissolve the fabric whereupon the water and dissolved fabric are subjected to disposal.

8 Claims, No Drawings

METHOD OF PRODUCING HOT WATER SOLUBLE GARMENTS AND LIKE FABRICS

The present application is a continuation of applicant's application Ser. No. 08/618,008 filed Mar. 18, 1996 abandoned, which is a continuation of application Ser. No. 08/299,760, filed Sep. 1, 1994 pending, which is a continuation of application Ser. No. 08/055,083, filed Apr. 29, 1993 abandoned, which is a continuation-in-part of application Ser. No. 07/881,685, filed May 12, 1992, U.S. Pat. No. 5,207,837 which is a continuation-in-part of application Ser. No. 07/683,290, filed Apr. 10, 1991 abandoned.

TECHNICAL FIELD OF THE INVENTION

The present invention involves a method of producing thermoplastic materials capable of being disposed after use. Specifically, garments produced according to this invention are composed of non-woven, woven, knitted or otherwise formed film or fabric of thermoplastic polymer or fiber which are water soluble at temperatures only above approximately normal human body temperature (37° C.).

BACKGROUND OF THE INVENTION

Hospital patient care generates considerable quantities of infectious medical waste in primary and acute care facilities. There has been a general conversion from reusable, cleanable items, to disposable items over the last three decades. These conversions were made to promote antiseptic techniques in patient care and to decrease the potential for cross-infections between patients, staff and the general public. Recent federal and state government regulations such as the Medical Waste Tracking Act of 1988 and OSHA Medical Facility rules have resulted in a substantial increase in medical waste that must be classified as "infectious."

When a patient is admitted to a hospital, the patient produces approximately 55 pounds of medical waste per day. Approximately 20% of this waste is infectious. The current stated objective of the American Hospital Association and the Centers for Disease Control is to treat medical waste as soon as it is generated. Both organizations recognize that medical waste is primarily an occupational hazard for health care workers and not an environmental problem. The best way to deal with infectious medical waste is to disinfect it at the point of generation and dispose of the treated medical waste with minimum handling and storage on premises.

The need for an effective way to dispose of medical waste has been highlighted by the amendment made to 29 C.F.R. §1910.1030 which provides for the federal regulation under the Occupational Safety And Health Act, 29 U.S.C. 655, 657 to control bloodborne pathogens. Specifically, the Act calls for the establishment of an exposure control plan, the containment of specimens of blood or other potentially infectious materials and the general tightening of precautionary measures to minimize the spread of disease. A safe and effective way to dispose of hospital waste in the form of soiled garments and apparel would greatly facilitate compliance with the above-referenced Act.

As a result, consumption of medical disposable woven or non-woven products has been growing at a rate of approximately 10% a year. In 1988, sales totaled approximately 1.155 Billion Dollars. It is projected that by 1992, sales of medical disposable non-woven products will reach 1.54 Billion Dollars.

Disposable medical fabrics are generally currently composed of thermoplastic fibers such as polyethylene, polypropylene, polyesters, polyamides and acrylics. These fabrics can also include mixtures of thermoset fibers such as polyamides, polyarimids and cellulosics. They are typically 10–100 grams per square yard in weight and can be woven, knitted or otherwise formed by methods well known to those in the textile arts while the non-wovens can be thermobonded, hydroentangled, wet laid or needle punched and films can be formed by blow or cast extrusion or by solution casting.

Although there is clearly a benefit in the use of disposables in the medical arts by avoiding the necessity of human contact with medical waste which is necessary in the cleaning of comparable reusables, non-biodegradable disposables are posing a problem which is only now being recognized. Landfill sites are becoming increasingly burdened with disposables which do not biodegrade for hundreds of years, if ever. As landfill sites become fully exploited, new sites must be found which are rightfully opposed by residents located proximate to proposed site locations.

It is clear that others have produced useful articles which at least break down or are caused to change their physical confirmation when subjected to hot aqueous solutions. For example, U.S. Pat. No. 3,314,809 teaches the production of transparent flexible films from hydroxypropyl cellulose which is taught to be "insoluble in water until the water reaches a temperature of about 60° C." However, hydroxypropyl cellulose, unlike polyvinyl alcohol, does not solubilize in water but simply breaks down forming a cellulose derivative residue.

The prior art has recognized uses for polyvinyl alcohol compositions in the manufacture of water soluble useful articles. For example, U.S. Pat. No. 3,413,229 teaches the production of water soluble bags or pouches from which packets or the like are produced containing such materials as detergents, bleaches, insecticides, medicinals, chemicals, dyes, pigments, industrial additives and other materials. It is taught that the contents of the packets are dispersed merely by dropping the packets into water whereupon the bags dissolve and release their contents into aqueous dispersions. However, the referenced patent teaches the production of such films which are both hot and cold water soluble.

Additional references, such as U.S. Pat. No. 3,859,125 teach the production of layered articles which include coatings of polyvinyl alcohol. The subject reference teaches coating polyvinyl alcohol on a paper membrane whereby it is taught that the coated paper is soluble in either high or low temperature water. Again, it is incorrect to believe that a cellulose sheet material would be "soluble" in an aqueous solution. At best, cellulose merely disperses. Similarly, U.S. Pat. No. 4,343,133 teaches the coating of polyvinyl alcohol onto a non-woven fiber sheet impregnated with latices of polyvinyl acetate in the manufacture of a premoistened towelette which can be disposed of by flushing in plain water without danger of clogging a plumbing system.

There has been the teaching of various medical related products which are generally in the form of articles coated with polyvinyl alcohol employed to enhance disposal. For example, European Patent Application No. 87310534.0 (Publication No. 0272816) teaches the production of an ostomy pouch which can be disposed of in a toilet bowel. The pouch is constructed from laminants of water swellable cold water insoluble films and water-resistant tissue paper. Similarly, U.K. Patent Application No. 2211088 teaches the production of a liner for a bed pan or urine bottle made of polyvinyl alcohol. It is taught that the liner may be disposed of by treatment with water at a temperature above that which it dissolves.

Both U.K. Patent No. 1,187,690 and Japanese Patent No. 72041741 teach the production of stand alone polyvinyl alcohol films which are water soluble. The U.K. patent teaches the production of hospital bags and packing material for such products as detergents and agricultural chemicals while the Japanese patent teaches the use of polyvinyl alcohol films to make laundry bags which dissolve releasing soiled garments contained therein. However, neither reference teaches the unique films of the present invention which can be configured into useful garments and like materials and which are soluble in aqueous solutions only above a threshold value.

It is thus an object of the present invention to provide a method of disposing of garments, linens, drapes, towels and other useful articles after use while avoiding additional burdens being placed upon landfill disposal sites.

It is yet a further object of the present invention to provide a method of disposing of garments, linens, drapes, towels and other useful articles after use such that the garment can be solubilized and medical waste substantially sterilized in a single operation.

These and further objects will be more readily appreciated while considering the following disclosure and appended claims.

SUMMARY OF THE INVENTION

The present invention involves a method of producing garments, films and fibers which can be disposed of after use which comprises providing the garments as sheets or as woven, non-woven, knitted or otherwise formed fabric of thermoplastic polymer or fiber. The polymer or fabric garments are water soluble only at temperatures above approximately the normal body temperature (37° C.). The garments, linens, drapes, towels and other useful articles composed of said polymer formulation are subjected to water at a sufficient temperature to substantially dissolve the garments whereupon the water and dissolved polymer are subjected to disposal.

DETAILED DESCRIPTION OF THE INVENTION

The present invention deals with the manufacture of garments, films and fibers configured into such articles as drapes, towels, covers, overwraps, gowns, head coverings, face masks, shoe coverings, CSR wraps, sponges, dressings, tapes, underpads, diapers, wash cloths, sheets, pillow covers, napkins and woven, non-woven, or otherwise formed fabric. Such products are generally employed in the medical industry both in hospitals, outpatient facilities and home environments.

Many of these products generally come into contact with human bodily fluids and their disposal and disinfection has become a matter of major concern in light of the lack of biodegradability of prior products and the potential spread of human fluid-born diseases such as hepatitis B and AIDS.

In order to cope with these difficulties, it is proposed that polymer or fabric employed in the manufacture of such items be composed of polymer films and/or fibers which are soluble in hot aqueous baths, including water, either alone or with the addition of surfactants, salts and bleaches above 37° C. and preferably above 50° C. Such fibers or sheets would be insoluble in cold to warm baths below 37° C., the average temperature of the human body. Ideally, the polymer or fabric would be soluble in baths only above 50° C., and, most preferably the polymer or fabric garments would be soluble only in aqueous media between 80° C. to 90° C.

Garments which are soluble in aqueous media below 37° C. are useless as inadvertent secretion of bodily fluids such as blood and urine would cause the polymer to solubilize. Working with polymer which dissolves only at higher temperatures such as above 50° C. or, ideally between 80° C. and 90° C. would prevent inadvertent solubilization yet remain ideal in practicing the present invention. It is contemplated that disposal in a hot water bath such as a washing machine at or near the boiling point of water dedicated solely to solubilizing garments, linens, drapes, towels and other useful articles produced herein would also be an effective disinfecting media. As such, two objectives would be accomplished, namely, that the polymer or sheets would be disinfected and would be solubilized for disposal through the sewer system. Not only would this lessen the burden now being imposed upon current landfill sites but liquid sewer disposal would prove a comparative low cost technique in ridding the user of such used garments.

Polymer or sheet materials useful in practicing the present method comprise polyvinyl alcohol with or without acetyl groups, cross-linked or uncross-linked. The garments are comprised of polyvinyl alcohol homopolymer that has been highly crystallized by post drawing or heat annealing. Ideal for use in the present invention would be a highly crystallized, at least approximately 98% saponified polyvinyl acetate. Commercially, polyvinyl alcohol sold under the trademark Vinex 1003™ and 1002™ by Air Products could be used herein. Useful fibers are typically 0.5 denier to 5.0 denier and are preferably from 1.0–2.0 denier and most preferably sized at 1.2–1.5 denier. A commercially available product for use in the present invention is either type T-B (VEE 1290) or type T-5 (VPB 101) which are each available from Kuralon as its PVA fiber. This material is sold in 44 mm lengths. The T-B product is sized at 1.2 denier while the T-5 product is sold in 38 mm staple lengths of 1.5 denier.

The fabric useful in practicing the present invention can be constructed by any well known technique for making woven, non-woven, knitted or otherwise formed fabric. Such non-woven techniques useful in practicing the present invention include spun bonding, melt blowing or wet laying, hydroentangling with cold water and/or thermally bonding with 30–70% of the surface melted to form, for example, a diamond pattern. When products, such as diapers, are configured of sheets of suitable thermoplastic material, the sheets are approximately 1 to 6 mils in thickness and more preferably 1 to 3 mils in thickness and most preferably approximately 1.5 mils in thickness. Suitable non-woven fabric or sheets are approximately from 15 g/yd$^2$ to 200 g/yd$^2$ in weight and more preferably from 20 g/yd$^2$ to 70 g/$^2$ and most preferably from 25 g/yd$^2$ to 80 g/yd$^2$. Knitted or woven fabrics are approximately 50% heavier as needed for binding tapes, cuffs and related appendages.

As noted in U.K. Patent No. 1,187,690, it is desirable to maintain a minimum level of moisture content of polyvinyl alcohol pellets prior to melt extrusion. The reference teaches that if moisture content of a film composition exceeds two percent by weight, steam evolves during the melt extrusion leading to the formation of fine holes or cavities in the film.

However, while the present invention also contemplates drying to a level of approximately 0.5% (wt.) water or less the polyvinyl alcohol pellets before extrusion and, subsequent to the film formation, moisture is reintroduced back into the film to prevent brittleness and maintain usefulness. It is contemplated that the final PVA film have between 1.5 to 15% (wt.), preferably 5 to 10% (wt.) and most preferably approximately 7.5% (wt.) moisture content.

In order to further enhance the usability of sheet material produced principally of polyvinyl alcohol, it is contemplated that an anti-blocking agent be employed to reduce hydrogen bonding between adjacent hydroxyl groups on separate sheets. Suitable anti-blocking agents are members selected from the group consisting of silicon dioxide ($SiO_2$) polymer, talc, calcium carbonate and fumed hydrophilic $SiO_2$. Such material should be employed between 0.1 to 5.0% (wt.) and most preferably between 2 to 3% (wt.) based upon the weight of the polyvinyl alcohol.

As noted previously, polymer or sheet material useful in practicing the present invention is comprised of polyvinyl alcohol with or without acetyl groups, cross-linked or uncross-linked. It is proposed that the polyvinyl alcohol be substantially fully hydrolyzed, that is, having 98% or greater hydrolyzed acetyl groups.

For the sake of adequate mechanical strength, polyvinyl alcohol-based sheet material should have a degree of polymerization of at least 700 and no greater than approximately 1500. Ideally, such materials should have a degree of polymerization of approximately 900 and be substantially crystallized.

It is also noted that in producing polyvinyl alcohol resins from the saponification of polyvinyl acetate, impurities such as sodium acetate and sodium sulfate are found in the resin. To provide a suitable film material, such impurities must be kept below ½% (wt.) and preferably below ¼% (wt.) of the polyvinyl alcohol resin. This can be accomplished with a methanol water rinse or extraction.

To enhance the manufacture of suitable polyvinyl alcohol resin-based film materials, suitable quantities of a plasticizer are necessary. It is contemplated that up to 15% (wt.) of a suitable plasticizer such as glycerine or polyethylene glycol be employed to assist in providing a smooth melt extrusion from the polyvinyl alcohol-based pellets.

As examples the following fabric samples were manufactured on conventional thermal bonding equipment.

| I.D. | TL-0079.0 | 79.1 | 79.2 | 080.0 | 0080.1 |
|---|---|---|---|---|---|
| Fibre | Kuralon T-5 PVA (1.5 denier, 38 mm staple length) | | | | |
| Pattern No. | 2 | 2 | 2 | 1 | 1 |
| Fabric Wt. (gms/sq. yd) | 27 | 44 | 47 | 35 | 43 |
| Thickness (mil) | 15 | 12 | 17 | 14 | 16 |
| Tensiles- (Grab-lbs) | | | | | |
| Dry MD | 8.3 | 11.7 | 16.6 | 13.8 | 16.1 |
| Wet MD | 3.2 | 4.8 | 4.6 | 3.1 | 6.0 |
| Dry CD | 2.0 | 2.3 | 4.3 | 3.8 | 5.2 |
| Wet CD | 1.0 | 1.5 | 1.7 | 1.3 | 2.3 |
| Elongation (%) | | | | | |
| Dry MD | 11 | 10 | 12 | 12 | 11 |
| Dry CD | 48 | 30 | 38 | 19 | 22 |
| Mullen Burst (psi) | | | | | |
| Dry | 11 | 15 | 19 | 13 | 16 |
| Wet | 10 | 14 | 19 | 13 | 15 |
| Hanle-O-Meter (gms) | 84 | 244 | 432 | 173 | 244 |
| Trap Tear- | | | | | |
| MD | 1.7 | 2.1 | 3.5 | 2.7 | 2.9 |
| CD | 0.4 | 0.4 | 0.8 | 0.6 | 0.7 |

It was found that the above-manufactured fabric displayed nearly identical physical properties similar to fabric manufactured from polyester and polypropylene. However, the fabric manufactured above was unaffected by cool or warm water (23°–37° C.) but when exposed to hot water (80°–90° C.), immediately dissolved.

It is oftentimes desirable that the film be colored with pigments or dyes such as azo or anthraquinone molecules. Useful dyes include acids, basics, disperse, reactives and vats. The pigments and dyes should be employed in an amount between approximately 0.25 to 3.0% (wt.) based upon the weight of the polymeric polyvinyl alcohol.

Surprisingly, it has been found that the incorporation of a water repellent within the polyvinyl alcohol film or fabric is quite a useful adjunct to minimize surface attack by liquid moisture at a temperature lower than that at which solubility occurs. It has been found that even with polyvinyl alcohol films and fabrics which become water soluble only at elevated temperatures, when exposed to water, the surface of such material tends to take on a slick "feel" and the use of water repellents tends to minimize this effect. Suitable repellents include fluorocarbons offered by the Minnesota Mining and Manufacturing Co. sold under its trademarks FC 824 and 808. These materials are useful in the range of between 0.1 to 2.0% (wt.) based upon the weight of the polyvinyl alcohol polymer.

I claim:

1. A method of producing thermoplastic polymer film of polyvinyl alcohol in the form of articles comprising at least one member selected from the group consisting of drapes, towels, covers, overwraps, gowns, head covers, face masks, shoe coverings, CSR wraps, sponges, dressings, tapes, underpads, diapers, washcloths, sheets, pillow covers and napkins, said thermoplastic polymer film of polyvinyl alcohol being soluble only at temperatures above 37° C., said thermoplastic polymer film being produced from pellets of polyvinyl alcohol, said pellets having an initial water content, said method comprising the steps of:

reducing said initial water content of said pellets to a level no greater than approximately 0.5% (wt.) prior to melt extrusion;

melt extruding pellets of polyvinyl alcohol to produce a film of polyvinyl alcohol;

incorporating within said pellets an anti-blocking agent in an amount between approximately 0.1 to 5.0% (wt.); and, subsequent to said melt extrusion, increasing the water content of said film of polyvinyl alcohol to a level between approximately 5–10% (wt.).

2. The method of claim 1 wherein said film of polyvinyl alcohol is made from a process selected from the group consisting of blow extrusion, cast extrusion and solution casting.

3. The method of claim 1 wherein said polyvinyl alcohol film includes a water repellent agent.

4. The method of claim 3 wherein said water repellent agent is contained within said polymeric film in an amount between approximately 0.1 to 2.0% (wt.).

5. A method of producing thermoplastic polymer fabric of polyvinyl alcohol which is water soluble only at temperatures above 37° C., said fabric being produced from pellets of polyvinyl alcohol, said pellets having an initial water content, said method comprising the steps of melt extruding said pellets of polyvinyl alcohol to produce fabric of polyvinyl alcohol only after said water content has been reduced to a level no greater than approximately 0.5% (wt.), said pellets incorporating an anti-blocking agent in an amount between approximately 0.1 to 5.0% (wt.); and subsequent to said melt extrusion, increasing the water content of said fabric to a level between approximately 5 to 10% (wt.).

6. The method of claim 5 wherein said polyvinyl alcohol fabric includes a water repellent agent.

7. The method of claim 6 wherein said water repellent agent is contained within said polymeric fabric in an amount between approximately 0.1 to 2.0% (wt.).

8. The method of claim 5 wherein said water repellent agent is contained within said polymeric fiber in an amount between approximately 0.1 to 2.0% (wt.).

* * * * *